United States Patent [19]

Rossi

[11] 3,944,589
[45] Mar. 16, 1976

[54] α-CYCLOALKENYLPHENYL-FATTY ACID NITRILES

[75] Inventor: Alberto Rossi, Oberwil, Switzerland

[73] Assignee: Ciba-Geigy Corporation, Ardsley, N.Y.

[22] Filed: Apr. 3, 1974

[21] Appl. No.: 457,521

Related U.S. Application Data

[60] Division of Ser. No. 92,327, Nov. 23, 1970, Pat. No. 3,822,309, which is a continuation-in-part of Ser. No. 862,443, Sept. 30, 1969, abandoned.

[30] Foreign Application Priority Data

| Oct. 11, 1968 | Switzerland | 15240/68 |
| Nov. 6, 1968 | Switzerland | 16569/68 |
| May 8, 1969 | Switzerland | 7083/69 |
| Aug. 21, 1969 | Switzerland | 12707/69 |
| Feb. 11, 1970 | Switzerland | 1985/70 |
| May 25, 1970 | Switzerland | 7728/70 |
| June 15, 1970 | Switzerland | 89990/70 |
| June 22, 1970 | Switzerland | 9481/70 |

[52] U.S. Cl. ..... 260/465 K; 260/465 E; 260/465 F; 260/465 G
[51] Int. Cl.² ............... C07C 121/66; C07C 121/75; C07C 121/78
[58] Field of Search ......... 260/465 K, 465 E, 465 F, 260/465 G

[56] References Cited
UNITED STATES PATENTS
3,526,653  9/1970  Shen et al. .......................... 260/465

*Primary Examiner*—Lewis Gotts
*Assistant Examiner*—Dolph H. Torrence
*Attorney, Agent, or Firm*—Joseph G. Kolodny; Theodore O. Groeger; John J. Maitner

[57] ABSTRACT

Compounds of the formula

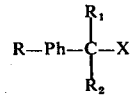

in which X represents a free carboxyl group or in the second place an esterified or amidated carboxyl group; R represents a 1-cycloalkenyl residue; Ph represents an ortho-phenylene residue or especially a para-phenylene residue; and $R_1$ and $R_2$ each represents a hydrogen atom or a monovalent or together a divalent aliphatic or araliphatic hydrocarbon residue, e.g. the α-[p-(1-cyclohexenyl)-phenyl]-propionic acid, are useful as analgetic and antiinflammatoric agents.

3 Claims, No Drawings

α-CYCLOALKENYLPHENYL-FATTY ACID NITRILES

CROSS-REFERENCES TO OTHER APPLICATIONS

This application is a division of copending application Ser. No. 92,327, filed Nov. 23, 1970, now U.S. Pat. No. 3,822,309, which, in turn, is a continuation-in-part of my copending application Ser. No. 862,443, filed Sept. 30, 1969 now abandoned.

SUMMARY OF THE INVENTION

The present invention is concerned with new α-phenyl-fatty acid compounds of the formula (I) 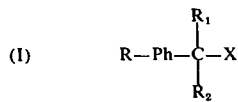

in which X represents a free carboxyl group or in the second place an esterified or amidated carboxyl group; R represents a 1-cycloalkenyl residue; P$h$ represents an ortho-phenylene residue or especially a para-phenylene residue; and $R_1$ and $R_2$ each represents a hydrogen atom or a monovalent or together a divalent aliphatic or araliphatic hydrocarbon residue, and their salts, as well as pharmaceutical preparations containing those compounds and a process for treating pain and inflammation which consists in administering to a warm blooded being such pharmaceutical preparations.

The 1-cycloalkenyl residues may be unsubstituted or contain one or several substituents. They consist, for example, of 4 to 8, especially 5 to 7, cyclic members, such as possibly mono- or polysubstituted 1-cyclobutenyl or 1-cyclooctenyl residues and especially 1-cyclopentenyl, 1-cyclohexenyl or 1-cycloheptenyl residues. Suitable substituents are, for example, aliphatic hydrocarbon residues, especially those mentioned below, primarily lower alkyl, alkoxy, alkenyloxy, hydroxyl, oxo or primary, secondary or tertiary amino groups, which may be substituted by the residues mentioned below for the carbamyl groups.

The phenylene residues P$h$ may be unsubstituted or contain one, two or more substituents, for example the following: Alkyl residues such as lower alkyls, especially those mentioned below, alkoxy residues, halogen atoms, trifluoromethyl groups or amino, nitro or hydroxyl groups.

Bivalent aliphatic hydrocarbon residues are, for example, alkylidene residues, such as lower alkylidene residues, especially methylidene or ethylidene residues.

Suitable monovalent aliphatic or araliphatic hydrocarbon residues are, for example, alkyl, alkenyl, alkinyl, aralkyl or aralkenyl groups, and especially those groups in which the aliphatic residues are lower ones and contain, for example, six carbon atoms at most.

Lower alkyl residues are, for example, methyl, ethyl, propyl or isopropyl groups, or linear or branched butyl, pentyl or hexyl residues bound in any desired position.

Lower alkenyl residues are, for example, allyl or methallyl residues.

A lower alkinyl residue is in the first place a propargyl residue.

Lower aralkyl and aralkenyl residues are more especially phenyl-lower alkyl and phenyl-lower alkenyl residues.

As phenyl-lower alkyl residues there may be mentioned, for example, 1- or 2-phenylethyl or benzyl residues whose phenyl nucleus may be substituted, for example, by lower alkyl or alkoxy groups, halogen atoms, trifluoromethyl groups or similar residues.

Phenyl-lower alkenyl residues are, for example, 1- or 2-phenylethenyl residues or cinnamyl residues whose phenyl nucleus may be substituted like the phenyl-lower alkyl residues.

Alkoxy residues are especially lower alkoxy residues, for example, methoxy, ethoxy, propoxy, isopropoxy, butoxy or amyloxy groups; specially suitable halogen atoms are fluorine, chlorine or bromine atoms.

Esterified carboxyl groups are especially those which are esterified with aliphatic, cycloaliphatic or araliphatic alcohols. Particularly suitable esterifying alcohols are lower alkanols, cycloalkanols or phenylalkanols which may contain further substituents, for example methanol, ethanol, propanols, butanols, hexanols, cyclopentanols, cyclohexanols or phenyl-lower alkanols which may be substituted for instance as shown above for the phenyl-lower alkyl residues, such as benzyl alcohols or phenylethanols.

Substituents of aliphatic alcohols are especially amino groups, preferably amino groups which are substituted as shown below for the amide groups, and are primarily di-lower alkylamino groups, for example dimethylamino or diethylamino groups, or piperidino groups.

Substituents of aliphatic alcohols are especially hydroxy groups which can also be bonded to ketal or acetal groupings by ketones or aldehyds. Ketones and aldehydes are in this context chiefly aliphatic ketones and aldehydes, above all lower alkanones and alkanals such, for example, as acetone, formaldehyde or acetaldehyde.

The amide nitrogen atom in the amidated carboxyl groups (carbamyl groups) is unsubstituted, mono- or disubstituted, for example, by preferably lower residues of aliphatic character which contain, for example, not more than 8 carbon atoms and which may be interrupted by hetero atoms, such as oxygen, nitrogen or sulphur atoms and/or may be substituted by functional groups such as hydroxyl, amino or mercapto groups or halogen atoms. As amide substituents there may be mentioned, for example, alkyl, alkenyl or alkylene residues which may be interrupted by oxygen, sulphur or nitrogen atoms and/or may be substituted by functional groups such as hydroxyl, amino or mercapto groups or by halogen atoms. Especially suitable amide substituents are lower alkyls such as methyl, ethyl, propyl, isopropyl; linear or branched butyl, pentyl, hexyl or heptyl linked in any desired position; lower alkenyl residues for instance allyl or methallyl; lower alkylene residues, for example butylene-(1,4), pentylene-(1,5), hexylene-(1,6) or heptylene-(2,6); cycloalkyl or cycloalkyl-alkyl residues or corresponding residues interrupted by the said hetero atoms, for example lower alkoxyalkyl, alkylmercaptoalkyl or mono- or dialkyl-aminoalkyl residues, for example 2-methoxy-ethyl, 2-ethoxyethyl, 3-methoxypropyl, 2-methylmercapto-ethyl, or dimethyl-, methylethyl- or diethylaminoalkyl groups, alkyleneaminoalkyl groups or oxa-, aza- or thia-alkyleneamino-alkyl groups, in which the alkylene or oxa-, aza- or thia-alkylene residues may be, for example, those mentioned below, or oxa-, aza- or thia-alkylene residues such as 3-oxa-, 3-aza- or 3-thia-pentylene-(1,5), 3-methyl-, 3-ethyl-3-aza-hexylene-(1,6), 3-azahexylene-(1,6) or 4-methyl-4-aza-heptylene-(2,6) or residues of this type that are substituted by functional groups, such as 3-chlorethyl- or 3-hydroxyethyl-3-aza-pentylene-(1,5), phenyl or phenylalkyl residues which may be unsubstituted or whose phenyl residue may be substituted especially as shown above for the phenyl-lower alkyl residues.

The amino group of the amidated carboxyl group (carbamyl group) is more especially a free or a mono- or di-lower alkylated amino group or a possibly C-lower alkylated pyrrolidino, piperidino, morpholino, thiomorpholino, piperazino, N'-lower alkylpiperazino or N'-(hydroxy-lower alkyl)-piperazino group, for example the N'-methylpiperazino group or the N'-($\beta$-hydroxyethyl)-piperazino group or N'-phenyl-piperazino group, or an amino group substituted by a hydroxyl or amino group.

The new compounds possess valuable pharmacological properties, especially an analgesic (such as antinociceptive) and an anti-inflammatory action. Thus, in the Writhing test on the mouse, on oral administration of 1 to 200, especially 10 to 200 mg/kg, they display a distinct antinociceptive action and in the kaolin oedema text on the rat paw or oral administration of a dose from 1 to 200 mg/kg a distinct anti-inflammatory action. The new compounds therefore are useful as analgesic (such as antinociceptive and anti-inflammatory agents.

The new compounds are also valuable intermediates for the manufacture of other useful substances, especially of pharmacologically active compounds.

Thus, for example, the new compounds may be used for the manufacture of the corresponding cycloalkyl compounds described in the literature by reducing the 1-cycloalkenyl groups to cycloalkyl groups in the usual manner, for example, by catalytic reduction.

Because of their importance those compounds of the formula I should be mentioned, wherein $R_1$ stands for lower alkyl, $R_2$ stands for hydrogen or lower alkyl and X represents a carboxyl group esterified with glycerine, it being possible for the hydroxyl groups of the glycerine that do not participate in the ester bond to be bonded also to ketal or acetal groupings by ketones or aldehydes, above all lower alkanones or alkanals, such as acetone or formaldehyde.

There should be highlighted primarily those of the above described glycerineesters in which R represents the 1-cyclohexenyl residue and P$h$ denotes the para-phenylene residue, such as the $\alpha$-[p-(1cyclohexenyl)-phenyl]-propionic acid-2,3-0-isopropylidene-1-glycerine ester and the $\alpha$-[p-(1-cyclohexenyl)-phenyl]-propionic acid-1-glycerine ester.

Special mention deserve the compounds of the general formula (II) 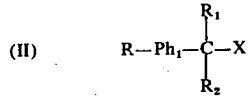

in which R and X have the above meanings, each of the radicals $R_1$ and $R_2$ represents a hydrogen atom, an alkyl, alkenyl, alkinyl, aralkyl or aralkenyl residue or both radicals together represent an alkylidene residue and P$h_1$ represents an ortho-phenylene residue or especially a para-phenylene residue which is substituted by one or several alkyl or alkoxy residues, halogen atoms or trifluoromethyl groups or is preferably unsubstituted.

Of special importance are the compounds of the general formula (III) 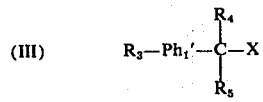

in which X has the above meaning, P$h_1$' stands for a p-phenylene residue optionally substituted as indicated just above, $R_3$ represents a 1-cycloalkenyl residue which may be substituted by one or several lower alkyl, lower alkenyl or phenyl residues or is preferably unsubstituted, and $R_4$ and/or $R_5$ each represents a hydrogen atom or primarily an alkyl or alkenyl residue.

Specially valuable because of their good antiinflammatory and analgesic (antinociceptive) action are the compounds of the formula (IV) 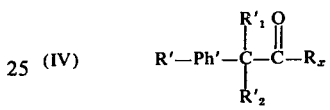

in which R' represents a 1-cycloalkenyl residue which is substituted by lower alkoxy groups and/or especially lower alkyl groups or is preferably unsubstituted and contains 5, 6 or 7 cyclic members; Ph' represents a para-phenylene residue which may be substituted by one or several trifluoromethyl groups, lower alkoxy groups, lower alkyl groups and/or especially by halogen atoms, or which is preferably unsubstituted; $R_1$' and $R_2$' each represents a lower alkyl residue or a hydrogen atom, and $R_x$ represents a lower alkoxy group such as methoxy or ethoxy, or a free amino group, a mono- or dilower alkylamino or -hydroxy-lower alkylamino group or a possibly C-lower alkylated pyrrolidino, piperidino, morpholino, N'-lower alkyl-piperazino, N'-hydroxy-lower alkyl-piperazino or N'-phenyl-piperazino or in the first place a hydroxyl group.

Specially valuable are the compounds of the formula (V) 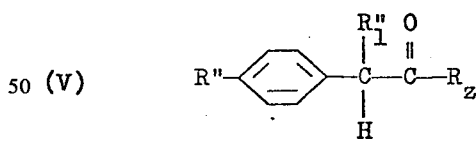

in which R'' represents a possibly lower alkylated 1-cyclopentenyl, 1-cyclohexenyl or 1-cycloheptenyl residue; $R_1$'' represents a lower alkyl, especially a methyl residue, or a hydrogen atom, and $R_z$ represents a hydroxyl group or in the second place a lower alkoxy group, especially one that contains at most 4 carbon atoms, or a free amino group, and more expecially the $\alpha$-[p-(1-cyclohexenyl)-phenyl]-propionic acid of the formula (VI) 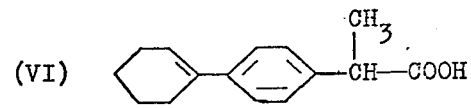

which, for example in form of its sodium salt on oral administration of a dose from 1 to 10 mg/kg in the Writhing test (phenyl-para-quinone) on the mouse displays a distinct antinociceptive action and in the kaolin paw oedema test on the rat on oral administration of a dose from 1 to 10 mg/kg has a distinct anti-inflammatory action.

Another compound which should be specially mentioned is the α-[3-chloro-4-(1-cyclohexenyl)-phenyl]-propionic acid of the formula

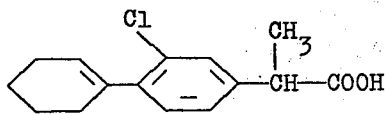

which, for example, an oral administration of a dose of 0.1 mg/kg in the Adjuvans arthritis test on rats, exhibits a distinct anti-arthritic action, and in the kaolin paw oedema test on rats on oral administration of a dose of 1 mg/kg, exhibits a marked anti-inflammatory action. This compound also exhibits a marked analgetic (antinociceptive) action, as can be shown in the Writhing-test (p-benzoquinone) on the mouse on oral administration of a dose of 1–10 mg/kg.

The new compounds are manufactured by known methods.

According to a preferred process in a compound of the formula (VII) 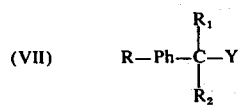

in which R, P$h$, $R_1$ and $R_2$ have the above meanings and Y represents a residue convertible into a free, esterified or amidated carboxyl group, Y is converted into a free, esterified or amidated carboxyl group.

The residue Y is, for example, the cyano group which can be converted into a free, esterified or amidated carboxyl group in the usual manner, for example by hydrolysis or alcoholysis.

The hydrolysis to the amidated or free carboxyl group is carried out in known manner, for example in the presence of a strong base, such as an alkali metal hydroxide, for example sodium or potassium hydroxide, or in the presence of a strong acid, for example a mineral acid such as hydrochloric acid, and, in the given case, in hydrolyzing to the free carboxyl group, with addition of an oxidant, such as nitrous acid.

The alcoholysis to an esterified carboxyl group is carried out in the usual manner, for example by reaction with an appropriate alcohol, for example in the presence of a mineral acid such as sulphuric acid, and advantageously in the presence of ammonium chloride.

It is also possible to perform the alcoholysis by preparing first an imino-ether, for example by reacting the nitrile with the alcohol in the presence of hydrogen chloride, preferably at low temperatures, e.g. −10° C. The so formed iminoether may then be subjected to mild hydrolysis, such as with dilute sulfuric acid under gentle warming, to yield the ester.

The residue Y may also be a functionally modified carboxyl group containing an oxo group, except an esterified or amidated carboxyl group, such as an acid halide, for example acid chloride grouping which can be converted into a free, esterified or amidated carboxyl group, for example by reaction with water, an alcohol, ammonia or an amine containing at least one hydrogen atom on the nitrogen atom, e.g. also hydrazine or hydroxylamine. The reaction is carried out in the usual manner, if desired in the presence of an acid acceptor, such as an organic or inorganic base, or if desired of a catalyst and/or oxidant, if desired in an acidic or neutral medium.

The residue Y may also be an aminothiocarbonyl group, such as a morpholino-thiocarbonyl group, which can be converted into the free carboxyl group by hydrolysis, for example in the manner described above for the hydrolysis of cyano groups, preferably by acid hydrolysis, for example in the presence of sulfuric acid and glacial acetic acid.

Y may also represent a residue convertible into a carboxyl group by oxidation, such as a formyl group or a reactive derivative of a formyl group, such as a hydrate, and may be converted into a carboxyl group by oxidation. Suitable oxidants for the oxidation of the formyl group are, for example, silver oxide in an alkali, for example in sodium hydroxide solution.

Substituents in resulting compounds can be introduced, modified or eliminated to suit the definition of the final products.

Thus, for example, in a resulting compound residues X can be converted into one another.

Esterified carboxyl groups and amidated carboxyl groups (that is to say carbamyl groups) can be converted into free carboxyl groups in the usual manner, for example by hydrolysis, preferably in the presence of a strong base or strong acid, for example those mentioned above. If desired, an oxidant, such as nitrous acid, may be used in the hydrolysis of carbamyl groups.

Free or esterified carboxyl groups can also be converted into carbamyl groups in the usual manner, for example by reaction with ammonia or with an amine containing at least one hydrogen atom on the nitrogen atom, e.g. also hydrazine or hydroxylamine and possibly dehydratization of the intermediately formed ammonium salt.

Free carboxyl groups can be esterified in the usual manner, for example by reaction with an appropriate alcohol, advantageously in the presence of an acid such as a mineral acid, for example sulphuric or hydrochloric acid, or in the presence of a water-binding agent, such as bicyclohexyl-carbodiimide, or by reaction with an appropriate diazo compound, for example with a diazoalkane. Esterification may also be performed by reacting a salt of the acid, for example the sodium salt, with a reactively esterified alcohol, for example a halogenide, such as the chloride.

Free carboxyl groups can also be converted, for example in the usual manner, into acid halide or anhydride groupings, for example by reaction with a halide of phosphorus or sulphur such as thionylchloride, phosphorus pentachloride or tribromide, or with an acid halide such as a chloroformic acid ester. The acid anhydride or halide groups can then be converted into esterified carboxyl or carbamyl groups respectively in the usual manner, by reaction with suitable alcohols, if desired in the presence of an acid acceptor, such as an organic or inorganic base, or with ammonia.

Furthermore, substituents $R_1$ and/or $R_2$ respectively can be introduced into resulting compounds in which $R_1$ and/or $R_2$ are hydrogen atoms. For instance a corresponding compound, in the first place an ester or an amide, may be converted into the α-metal salt, for example by reaction with a strong base such as an amide, hydride or hydrocarbon compound of an alkali metal, such as sodamide or sodium hydride or phenyl lithium or butyl lithium, and then reacted, preferably without isolation, with a reactive ester of an appropriate alcohol, for example an alcohol of the formula R₁OH or R₂OH respectively. Reactive esters are more especially those with strong inorganic or organic acids, preferably with hydrohalic acid such as hydrochloric, hydrobromic or hydriodic acid, with sulphuric acid or with arylsulphonic acids such as benzene-, p-toluene- or p-bromobenzene-sulphonic acid.

Depending on the reaction conditions and starting materials there may be obtained salt-forming final products in free form or in form of their salts which can be converted in the usual manner one into the other or into different salts. Thus, acid final products (that is to say such as contain a free carboxyl group) are obtained in free form or in form of their salts with bases. Resulting free acid compounds can be converted in the usual manner, for example by reaction with appropriate basic agents, into the salts with bases, especially therapeutically acceptable salts with bases, for example salts with organic amines or into metal salts. Suitable metal salts are in the first place alkali metal salts or alkaline earth metal salts, such as sodium, potassium, magnesium or calcium salts. From the salts free acids can be liberated in the usual manner, for example by reaction with an acid agent. Final products with a basic character can likewise be obtained in free form or in the form of their salts. The salts of the basic final products can be converted into the free bases in known manner, for example with alkalies or ion exchange resins. When the free bases are reacted with organic or inorganic acids, especially acids capable of forming therapeutically useful salts, they give rise to salts. As such acids there may be mentioned for instance the hydrohalic acids, sulphuric acids, phosphoric acids, nitric acid, perchloric acid; aliphatic, alicyclic, aromatic or heterocyclic carboxylic or sulphonic acids such as formic, acetic, propionic, succinic, glycolic, lactic, malic, tartaric, citric, ascorbic, maleic, hydroxymaleic or pyruvic acid; phenylacetic, benzoic, p-aminobenzoic, anthranilic, p-hydroxybenzoic, salicylic, p-aminosalicylic, embonic, methanesulphonic, ethanesulphonic, hydroxyethanesulphonic, ethylenesulphonic acid; halobenzenesulphonic, toluenesulphonic, napthalenesulphonic acids or sulphanilic acid; methionine, tryptophan, lysine or arginine.

These and other salts, for example the picrates, are also suitable for purifying the new compounds, for example by converting the free compounds into their salts, isolating the salts and reconverting them into the free compounds. In view of the close relationship between the new compounds in free form or in form of their salts what has been said above and hereinafter with reference to the free compounds concerns also the corresponding salts wherever possible and useful.

Depending on the chosen starting materials and reaction conditions and on the number of asymmetric carbon atoms the new compounds may be obtained as optical antipodes, racemates or isomer mixtures (for example racemate mixtures).

Resulting isomer mixtures (racemate mixtures) can be resolved into the two stereoisomeric (diastereomeric) pure isomers (for example racemates) on the basis of the physicochemical differences of the constituents in known manner, for example by chromatography and/or fractional crystallization.

Racemates obtained can be resolved into the diastereomers, from which the antipodes can be liberated by treatment with suitable agents. This resolution may be carried out in known manner, for example by recrystallization from an optically active solvent, or with the aid of microorganisms or by reaction of a free carboxylic acid with an optically active base capable of forming salts with the racemic compound and separation of the salts thus obtained, for example on the basis of their different solubilities. A particularly frequently used optically active base is, for example, the D- and L-forms of cinchonine. It is advantageous to isolate the more active of the two antipodes.

Resulting racemates of basic compounds can also be resolved into the diastereomers by reaction with an optically active acid capable of forming salts with the racemic compound and separation of the salts thus obtained, for example on the basis of their different solubilities, and from the diastereomers the antipodes can be liberated by treatment with suitable reagents. Particularly frequently used optically active acids are, for example, the D- and L-forms of tartaric acid, di-o-toluyltartaric acid, malic acid, mandelic acid, camphorsulphonic acid or quinic acid.

The invention includes also any variant of the present process in which an intermediate obtained at any stage thereof is used as starting material and any remaining step(s) is/are carried out or in which a starting material is formed under the reaction conditions, or a reactant may be used in form of a salt.

The reactions of this invention are advantageously carried out with starting materials that give rise to the final products in the groups specially mentioned above and in the first place to the specifically described or emphasized final products.

The starting materials are known or, insofar as they are new, they can be manufactured by known methods.

The nitriles of the formula

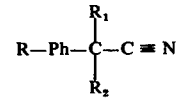

preferably used as starting materials are obtained, for example, when a compound of the formula

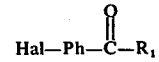

in which H*al* represents a halogen atom such as a chlorine or bromine atom, is converted into a corresponding ketal or, respectively, acetal, for example, a lower alkylene-ketal, such as an ethylene-ketal or a di-lower alkyl-ketal, such as a dimethyl-ketal, the resulting compound is converted with magnesium into the corresponding Grignard reagent which is then reacted with a corresponding cycloalkanone. In the resulting [1-hydroxy-cycloalkyl] compound the hydroxyl group is eliminated, advantageously in the presence of an acid, with formation of a 1,2-double bond and in the resulting compound of the formula

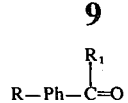

the oxo group is reduced to the hydroxyl group. The hydroxyl group is then converted in the usual manner, for example by reaction with a halide of phosphorus or sulphur such as phosphorus oxychloride or thionylchloride or a similar bromide, into a corresponding halogen atom which can then be converted into the cyano group by reaction with a salt of hydrocyanic acid such as sodium cyanide. Compounds in which $R_2$ is not hydrogen can be manufactured by introducing the residue $R_2$, for example into the nitrile, for instance in a manner similar to that described above for the esters and amides, via the α-metal salt and reaction with a reactive ester of an appropriate alcohol.

The compounds of the formula

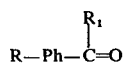

described above may be used also for preparing the starting materials of the formula VII wherein Y stands for an aminothiocarbonyl and both $R_1$ and $R_2$ stand for hydrogen. This is done by way of the well known Willgerodt reaction, using sulfur and ammonia or an amine, especially a secondary amine such as morpholine.

The new compounds can be used, for example, in form of pharmaceutical preparations that contain them in free form or in form of their salts, especially the therapeutically acceptable alkali metal salts, in conjunction or admixture with an organic or inorganic, solid or liquid pharmaceutical excipient suitable, for example, for enteral, parenteral or local administration. Suitable excipients are substances that do not react with the new compounds, for example water, gelatin, lactose, starches, stearyl alcohol, magnesium stearate, talcum, vegetable oils, benzyl alcohols, gums, propyleneglycols, white petroleum jelly or other known medicinal excipients. The pharmaceutical preparations may be, for example, tablets, dragees, capsules, suppositories, creams or ointments, or in liquid form solutions (for example elixirs or syrups), suspensions or emulsions. They may be sterilized and/or contain assistants such as preserving, stabilizing, wetting or emulsifying agents, solubilizers, salts for regulating the osmotic pressure or buffers. They may also contain further therapeutically valuable substances. The pharmaceutical preparations are formulated by known methods.

The following examples illustrate the invention.

EXAMPLE 1

A solution of 50.3 g of α-[para-(1-cycloheptenyl)-phenyl]-propionic acid nitrile and 26 g of potassium hydroxide in 400 ml of ethanol and 80 ml of water is refluxed for 36 hours. The ethanol is evaporated under reduced pressure and the residue dissolved in water. The aqueous solution is first extracted by agitation with ether, then acidified with concentrated hydrochloric acid, and extracted again with ether. The ethereal extracts are washed with water, dried over sodium sulfate, evaporated under reduced pressure and recrystallized from ether+petroleum ether to obtain α-[para-(1-cycloheptenyl)-phenyl]-propionic acid of the formula

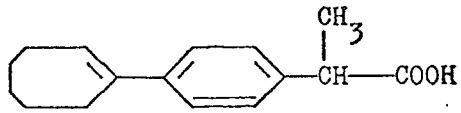

in the form of colorless crystals melting at 105°–107° C.

The sodium salt is obtained by dissolving this carboxylic acid in the calculated quantity of ethanolic sodium hydroxide solution and evaporation in vacuo. Its decomposition point is 229°–233° C.

The α-[para-(1-cycloheptenyl)-phenyl]-propionic acid nitrile used as starting material can be prepared as follows:

A well-stirred suspension of 14.6 g of magnesium chips which have been washed with chloroform and activated with iodine, in 150 ml of absolute tetrahydrofuran is mixed dropwise at 60° C with a solution of 97.6 g of 2-(para-bromo-phenyl)-2-methyl-1,3-dioxolan in 500 ml of tetrahydrofuran. The dropwise addition is made in such manner that after the onset of the reaction the temperature does not rise above 60° C. At the end, the batch is heated at 60° C for 30 minutes, the cooled to 20° C and treated dropwise with 67 g of cycloheptanone while stirring. The reaction mixture is heated at 50°–60° C for one hour, then evaporated. The residue is treated with ice and 200 ml of a saturated aqueous ammonium chloride solution. There follow extraction with ether, drying over sodium sulfate and evaporation. The residue is recrystallized from ether+λ petroleum ether to obtain 2-[para-(1'-hydroxycycloheptyl)-phenyl]-2-methyl-1,3-dioxolan as a colorless crystalline compound of melting point 78°–80° C.

A solution of 43 g of this compound in 240 ml of glacial acetic acid and 90 ml of 2N-hydrochloric acid is heated at 100° C for one hour. After cooling 300 ml of water are added and the whole extracted with ether, washed with 2N-sodiumbicarbonate solution, and the ethereal extracts are dried over sodium sulfate and evaporated. The oily residue is distilled in a high vacuum and gives para-(1-cycloheptenyl)-acetophenone as a viscous oil boiling at 140° C under a pressure of 0.04 mm of Hg.

A solution of 49 g of this ketone in 100 ml of methanol is stirred dropwise into a solution, cooled to 0° C, of 11 g of sodium borohydride in 500 ml of methanol and 100 ml of water. The reaction solution is stirred for another hour and a half at 5° to 10° C and then allowed to stand at room temperature for 16 hours. Finally, 600 ml of water are added and the batch is extracted with methylene chloride, dried over sodium sulfate and evaporated. In this manner, 1-hydroxy-1-[para-(1-cycloheptenyl)-phenyl]-ethane is obtained as an oily, colorless residue.

49 g of this hydroxy compound are dissolved in 400 ml of absolute benzene, mixed with 28 ml of thionyl chloride and allowed to stand at room temperature for 2 hours, then evaporated under reduced pressure. A solution of the resulting 1-chloro-1-[para-(1-cycloheptenyl)-phenyl]-ethane in 100 ml of dimethylsulfoxide is stirred into a suspension, heated at 50°–60° C, of 26 g of sodium cyanide in 150 ml of dimethylsulfoxide. The reaction was allowed to proceed for another hour at this temperature, the batch is then cooled and mixed with 150 ml of water, followed by extraction with a 1:1 mixture of ether and ethyl acetate. The organic ether extracts are washed with water, dried over sodium sulfate and evaporated to give crude α-[para-(1- cycloheptenyl)-phenyl]-propionic acid nitrile in the form of a viscous brown oil which is suitable for the afore-described hydrolysis.

EXAMPLE 2

A solution of 27.5 g of α-[para-(1-cyclopentenyl)-phenyl]-propionic acid nitrile and 16.5 g of potassium hydroxide in 200 ml of ethanol and 40 ml of water is refluxed for 30 hours. The batch is then evaporated under reduced pressure, the residue dissolved in water and the solution extracted with ether. The clear aqueous solution is acidified with 5N-hydrochloric acid and extracted with ether. The ethereal extracts are dried over sodium sulfate and evaporated. The solid residue is recrystallized from ether+petroleum ether, and α-[para-(1-cyclopentenyl)-phenyl]-propionic acid of the formula

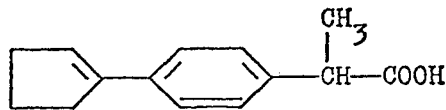

obtained in the form of colorless crystals melting at 137°–140° C.

The sodium salt is obtained by dissolving this carboxylic acid in the calculated quantity of ethanolic sodium hydroxide solution and precipitation with ether.

The α-[para-(1-cyclopentenyl)-phenyl]-propionic acid nitrile used as starting material can be prepared as follows:

A well-stirred suspension of 7.3 g of magnesium chips, which have been washed with chloroform and activated with iodine, in 150 ml of absolute tetrahydrofuran is treated dropwise at 60° C with a solution of 48.6 g of 2-(para-bromo-phenyl)-2-methyl-1,3-dioxolan in 100 ml of tetrahydrofuran. The dropwise addition is made in such manner that after the onset of the reaction the temperature does not rise above 60° C. Finally, the batch is heated at 60° C for 30 minutes, then cooled to 20° C, and stirred during the dropwise addition of 21.6 g of cyclopentanone. The reaction mixture is heated at 50–60°C for one hour, then evaporated, and the residue mixed with ice and 200 ml of saturated aqueous ammonium chloride solution. The batch is extracted with ether, the ethereal solution dried over sodium sulfate and evaporated. The residue is recrystallized from ether+petroleum ether, and 2-[para-(1'-hydroxy-cyclopentyl)-phenyl]-2-methyl-1,3-dioxolan obtained which melts at 90°–91°C.

A solution of 15 g of this compound in 80 ml of glacial acetic acid and 30 ml of 2-N-hydrochloric acid is heated at 100°C for 1 hour. After cooling, the solution is diluted with 200 ml of water and extracted with ether. The ether layers are washed with 2N-sodium bicarbonate solution, dried over sodium sulfate, and evaporated. The residue, on recrystallization from ether+petroleum ether, gives para-(1-cyclopentyl)-acetophenone melting at 100°–102°C.

A solution of 30 g of this ketone in 200 ml of methanol is added dropwise while stirring to a solution, cooled to 0°C, of 7.8 g of sodium borohydride in 300 ml of methanol and 60 ml of water. Stirring is continued for another hour and a half at 5°–10°C, the mixture allowed to stand for 16 hours, mixed with water and extracted with methylene chloride. The methylene chloride extracts are dried over sodium sulfate, evaporated, and the residue recrystallized from ether+petroleum ether to obtain 1-hydroxy-1-[para-(1-cyclopentenyl)-phenyl]-ethane of melting pont 90°–92°C.

Solution of 35.5 g of this hydroxy compound in 150 ml of absolute benzene is mixed with 21 ml of thionyl chloride and stirred for 2 hours at room temperature. The batch is then evaporated under reduced pressure, and the resulting crude, oily 1-chloro-1-[para-(1-cyclopentenyl)-phenyl]-ethane dissolved in 50 ml of dimethylsulfoxide and stirred into a suspension, heated at 50°–60°C, of 23 g of sodium cyanide in 400 ml of dimethylsulfoxide. The batch is kept at this temperature for one hour, then cooled, diluted with 300 ml of water, and extracted with a 1:1 mixture of ether and ethyl acetate. The organic extracts are washed with water, dried over sodium sulfate, evaporated, and the crude, oily α-[para-(1-cyclopentenyl)-phenyl]-propionic acid nitrile obtained which can be used for the above-described hydrolysis as it is.

EXAMPLE 3

A solution of 24 g of a mixture of α-[para-(6-methyl-1-cyclohexenyl)-phenyl]-propionic acid nitrile and α-[para-(2-methyl-1-cyclohexenyl)-phenyl]-propionic acid nitrile and 11 g of potassium hydroxide in 200 ml of ethanol and 70 ml of water is refluxed for 15 hours. The ethanol is evaporated under reduced pressure and the residue dissolved in water and extracted with ether. The aqueous solution is acidified with 5N-hydrochloric acid and extracted with ether. The oily ether-residue is dissolved in ether and treated with a solution of sodium ethanolate in ethanol which causes a mixture of the sodium salt of α-[para-(6-methyl-1-cyclohexenyl)-phenyl]-propionic acid and of the sodium salt of α-[para-(2-methyl-1-cyclohexanyl)-phenyl]-propionic acid of the formula

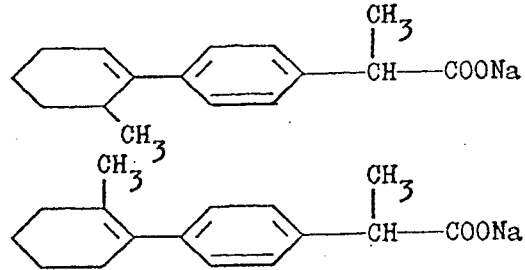

to precipitate. The mixture is isolated by filtration, washing with acetone+ether and drying under reduced pressure at 60°C.

The α-[para-(methyl-1-cyclohexenyl)-phenyl]-propionic acid nitrile mixture used as starting material can be prepared as follows:

A well-stirred suspension of 8.8. g of magnesium chips which have been washed with chloroform and activated with iodine, in 150 ml of absolute tetrahydrofuran is treated dropwise at 60°C with a solution of 23 g of 2-(para-bromo-phenyl)-2-methyl-1,3-dioxolan in 450 ml of absolute tetrahydrofuran. The dropwise addition is made in such manner that after the onset of the reaction the temperature does not rise above 60°C. The batch is finally heated at 60°C for another 30 minutes, then cooled to 5°C, and 41 g of 2-methylcyclohexanone then stirred in dropwise. The reaction mixture is heated at 50°–60°C for one hour, then filtered and evaporated in a rotary evaporator. The residue is treated with ice and a saturated aqueous ammonium chloride solution. The mixture is extracted with ether, dried over sodium sulfate and evaporated. The residue is recrystallized from ether+petroleum ether and 2-[para-(2'-methyl-1'-hydroxy-cyclohexyl)-phenyl]-2-methyl-1,3-dioxolan obtained which melts at 77°–80°C.

A solution of 33 g of this compound in 150 ml of glacial acetic acid is mixed with 80 ml of 2N-hydrochloric acid and heated at 100°C for one hour. The mixture is cooled, treated with 700 ml of water, extracted with 2 × 300 ml of petroleum ether, dried over sodium sulfate, and evaporated. The residue is distilled in a high vacuum, and a 7:3 mixture of para-(6-methyl-1-cyclohexenyl)-acetophenone and para-(2-methyl-1-cyclohexenyl)-acetophenone obtained as a faintly yellowish oil which boils at 130°–140°C under a pressure of 0.2 mm of Hg.

A solution of 23 g of the ketone mixture described above is added dropwise while stirring to a solution, cooled to 5°C, of 4 g of sodium borohydride in 200 ml of methanol and 40 ml of water. The mixture is stirred for another hour and a half at 5° to 10°C, then allowed to stand for 16 hours, treated with 600 ml of water, extracted with methylene chloride, dried over sodium sulfate and evaporated in vacuo. The residue is distilled in a high vacuum, and a mixture of 1-hydroxy-1-[para-(6-methyl-1-cyclohexenyl)-phenyl]-ethane and 1-hydroxy-1-[para-(2-methyl-1-cyclohexenyl)-phenyl]-ethane obtained as a colorless oil boiling at 120°–140°C under a pressure of 0.1 mm of Hg.

A solution of 23 g of this mixture in 200 ml of absolute benzene is allowed to stand at room temperature for 16 hours in the presence of 11.5 ml of thionyl chloride. The mixture is evaporated under reduced pressure, and the resulting crude oily mixture of 1-chloro-1-[para-(6-methyl-1-cyclohexenyl)-phenyl]-ethane and 1-chloro-1-[para-(2-methyl-1-cyclohexenyl)-phenyl]-ethane is dissolved in 30 ml of dimethylsulfoxide and the solution added dropwise while stirring to a suspension, heated at 50°C. of 18 g of sodium cyanide in 120 ml of dimethyl-sulfoxide. The reaction is allowed to proceed for another 2 hours at 70°–80°C, the batch then cooled and treated with 300 ml of water. The ethereal extract is evaporated and the residue is a 7:3 mixture of α-[para-(6-methyl-1-cyclohexenyl)-phenyl]-propionic acid nitrile and α-[para-(2-methyl-1-cyclohexenyl)-phenyl]-propionic acid nitrile which can be used as it is for the above-described hydrolysis.

EXAMPLE 4

A solution of 18 g of α-[para-(4-methyl-1-cyclohexenyl)-phenyl]-propionic acid nitrile and 9.2 g of potassium hydroxide in 120 ml of ethanol and 70 ml of water is refluxed for 24 hours. The ethanol is evaporated in a rotary evaporator under reduced pressure and the residue mixed with 400 ml of water, then extracted with ether. The aqueous solution is acidified with 2N-hydrochloric acid and extracted by agitation with ether. The ethereal solution is dried over magnesium sulfate and evaporated, and the residue is recrystallized from ether+petroleum ether to obtain α-[para-(4-methyl-1-cyclohexenyl)-phenyl]-propionic acid of the formula

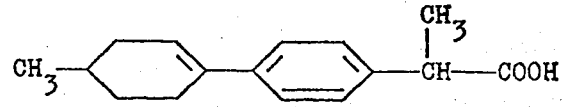

in the form of pale yellow crystals of melting point 100°–104°C.

The sodium salt is obatined by dissolving this carboxylic acid in the calculated quantity of ethanolic sodium hydroxide solution and precipitation with ether.

The α-[para-(4-methyl-1-cyclohexenyl)-phenyl]-propionic acid nitrile used as starting material can be prepared as follows:

A well-stirred suspension of 7.3 g of magnesium chips, which had been washed with chloroform and activated with iodine, in 150 ml of absolute tetrahydrofuran is treated dropwise at 60°C with a solution of 48.6 g of 2-(para-bromophenyl)-2-methyl-1,3-dioxolan in 100 ml of tetrahydrofuran. When the reaction has set in, the remainder of the solution is added dropwise, care being taken to keep the temperature from rising above 60°C. Finally, the batch is heated at 50°–60°C for another hour, then cooled to 20°C and treated dropwise with 34 g of 4-methyl-cyclohexanone. The reaction is allowed to proceed for another hour at 50°–60°C. The batch is evaporated and the residue mixed with ice and a saturated aqueous ammonium chloride solution. There follow extraction with ether, drying over magnesium sulfate and evaporation. The residue is recrystallized from ether+pentane to obtain 2-[para-(4'-methyl-1'-hydroxy-cyclohexyl)-phenyl]-2-methyl-1,3-dioxolan melting at 125°–127°C.

A solution of 15 g of this compound in 80 ml of glacial acetic acid is mixed with 30 ml of 2N-hydrochloric acid and heated at 100°C for one hour. Water is added and the batch extracted with ether. The ethereal solution is washed with 2N-bicarbonate solution and with water, dried over magnesium sulfate, and evaporated. The solid residue obtained is recrystallized from ether+petroleum ether to obtain para-(4-methyl-1-cyclohexenyl)-acetophenone melting at 50–52°C.

8.8 g of para-(4-methyl-1-cyclohexenyl)-acetophenone are stirred portionwise into a solution, cooled to 0°C, of 1.8 g of sodium borohydride in 80 ml of methanol and 15 ml of water. Stirring is continued at 5°–10°C for an hour and a half and at room temperature for 4 hours, 200 ml of water are added, and the batch then extracted with 3 × 100 ml of methylene chloride. The methylene chloride residue is recrystallized from petroleum ether and yields 1-hydroxy-1-[para-(4-methyl-1-cyclohexenyl)-phenyl]-ethane of melting point 65°–67°C.

A solution of 4.3 g of this compound in 60 ml of absolute benzene is stirred at room temperature for 2 hours with 2.5 ml of thionyl chloride. The batch is evaporated under reduced pressure, the crude, oily 1-chloro-1-[para-(4-methyl-1-cyclohexenyl)-phenyl]-ethane is dissolved in 20 ml of absolute dimethylsulfoxide, and the resulting solution is added dropwise to a suspension of 2.3 g of sodium cyanide in 30 ml of absolute dimethylsulfoxide. The batch is heated for 3 hours at 50°–60°C, then cooled, treated with 150 ml of water, and extracted with a 1:1 mixture of ether and ethyl acetate. The extract is washed with water, dried over magnesium sulfate, and evaporated. The brown, oily residue consists predominantly of α-[para-(4-methyl-1-cyclohexenyl)-phenyl]-propionic acid nitrile and can be used as it is for the hydrolysis described above.

EXAMPLE 5

A solution of 24 g of α-[para-(4-methoxy-1-cyclohexenyl)-phenyl]-propionic acid nitrile and 10 g of potassium hydroxide in 200 ml of ethanol and 70 ml of water is refluxed for 24 hours. The solution it then evapored under reduced pressure, the residue dissolved in water and extracted with ether, the aqueous phase is acidified with 5N-hydrochloric acid, and the oil that precipitates is extracted with ether. The oily ethereal residue is dissolved in ether, mixed with a solution of sodium ethanolate in ethanol after which the sodium salt of α-[para-(4-methoxy-1-cyclohexenyl)-phenyl]-propionic acid of the formula

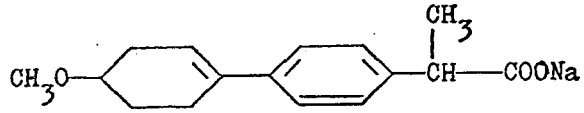

precipitates. It is isolated by filtration, washing with acetone+ether and drying in vacuum at 60°C.

The α-[para-(4-methoxy-1-cyclohexenyl)-phenyl]-propionic acid nitrile used as starting material can be prepared as follows:

A well-stirred suspension of 14.5 g of magnesium chips, which have been washed with chloroform and activated with iodine, in 150 ml of absolute tetrahydrofuran is treated dropwise at 60°C with a solution of 121 g of 2-(para-bromophenyl)-2-methyl-1,3-dioxolan in 500 ml of absolute tetrahydrofuran. The dropwise addition is made in such manner that once the reaction has set in the temperature does not rise above 60°C. At the end, the batch is heated at 60°C for 30 minutes, then cooled to 5°C, and 77 g of 4-methoxycyclohexanone are stirred in dropwise. The reaction mixture is heated at 50°-60°C for one hour, then filtered and evaporated in a rotary evaporator. The residue is treated with ice and a saturated aqueous ammonium chloride solution. The mixture is extracted with ether, dried over sodium sulfate and evaporated. The residue is recrystallized from ether+petroleum ether, and 2-[para-(4-methoxy-1-hydroxy-cyclohexyl)-phenyl]-2-methyl-1,3-dioxolan obtained which melts at 137°-140°C.

A solution of 55 g of this compound in 120 ml of glacial acetic acid is mixed with 20 ml of concentrated hydrochloric acid and 40 ml of water. The mixture is heated at 80°-90°C for 2 hours, cooled, mixed with 2000 ml of water, and extracted with ether. The ethereal residue is distilled in a high vacuum at 160°-170°C under a pressure of 0.1 mm of Hg. and finally recrystallized from petroleum ether to obtain para-(4-methoxy-1-cyclohexenyl)-acetophenone of melting point 40°-42°C.

To a solution, cooled to 5°C, of 4.5 g of sodium borohydride in 200 ml of methanol and 40 ml of water are added 24 g of the aforementioned ketone, the mixture is stirred for 2 hours at 5°-10°C, mixed with 500 ml of water, extracted with methylene chloride, and evaporated. The oily residue is distilled in a high vacuum at 160°-180°C (0.1 mm Hg.). A solution of 24 g of the resulting oily 1-hydroxy-1-[para-(4-methoxy-1-cyclohexenyl)-phenyl]-ethane in 250 ml of absolute benzene is treated with 12 ml of thionyl chloride and stirred at room temperature for 3 hours. After evaporation under reduced pressure, the crude, oily 1-chloro-1-[para-(4-methoxy-1-cyclohexenyl)-phenyl]-ethane is added to a suspension, heated at 50°C, of 18 g of sodium cyanide in 100 ml of dimethylsulfoxide. The reaction is allowed to proceed for another hour at 65° C, the batch then cooled, treated with 400 ml of water, and extracted with ether. The ethereal residue is crude α[para-(4-methoxy-1-cyclohexenyl)-phenyl]-propionic acid nitrile and it can be used as it is for the afore-described hydrolysis.

EXAMPLE 6

A solution of 9.5 g of α-[p-(1-cyclohexenyl)-phenyl]-propionitrile in a solution of 5 g of potassium hydroxide in 150 ml of ethanol and 50 ml of water is refluxed for 24 hours. The ethanol is evaporated under vacuum and the residue mixed with 200 ml of water. The insoluble phase is filtered off, mixed with active carbon and filtered off. The clear aqueous solution is acidified with 2N-hydrochloric acid and extracted with methylenechloride. The methylenechloride solution is dried over magnesium sulphate and evaporated and the residue recrystallized from ether+petroleum ether, whereupon α-[p-(1-cyclohexenyl)-phenyl]-propionic acid of the formula

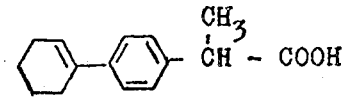

is obtained in colourless crystals melting at 106°-108°C. The sodium salt is obtained by dissolving this carboxylic acid in the calculated quantity of ethanolic sodium hydroxide solution and evaporation under vacuum; decompositions point: (245°C) 248°-250°C.

The α-[p-(1-cyclohexenyl)-phenyl]-propionitrile used as starting material in this Example is prepared thus:

A well-stirred suspension of 9.8 g of magnesium chips (previously washed with chloroform and activated with iodine) in 150 ml of absolute tetrahydrofuran is mixed dropwise at 60°C with a solution of 96 g of 2-(p-bromophenyl)-2-methyl-1,3-dioxolan in 150 ml of tertahydrofuran. The dropwise addition is regulated so that the temperature does not rise above 60°C once the reaction has set in. Towards the end the batch is heated for 30 minutes at 60°C, then cooled to 5°C and 35 g of cyclohexanone are stirred in dropwise. After having heated the reaction mixture for 1 hour at 50°-60°C, it is filtered and evaporated in a rotary evaporator. The residue is mixed with ice and a saturated aqueous ammoniumchloride solution, extracted with ether, dried over magnesium sulphate and evaporated. The residue is recrystallized from ether+petroleum ether and yields 2-[p-(1'-hydroxy-1'-cyclohexyl)-phenyl)]-2-methyl-1,3-dioxolan melting at 117°-118°C.

A solution of 80 g of this compound in 200 ml of glacial acetic acid is mixed with 30 ml of concentrated hydrochloric acid and 50 ml of water, and the mixture is heated for 3 hours on a waterbath at 80°C. Water is added until no more turbidity appears, and the settled-out crystals are filtered off and dried and recrystallized from petroleum ether, to yield p-(1-cyclohexenyl)-acetophenone melting at 76°-77°C.

A solution of 7 g of sodium borohydride in 300 ml of methanol and 80 ml of water is cooled to 5°C and 50 g of p-(1-cyclohexenyl)-acetophenone are stirred in portionwise. The batch is stirred on for 2 hours at room temperature, the solution is concentrated to half its volume in a rotary evaporator, mixed with 1 litre of water and extracted with 3 × 500 ml of methylenechloride. The methylenechloride residue is recrystallized from petroleum ether and furnishes 1-hydroxy-1-[p-(1-cyclohexenyl)-phenyl]-ethane melting at 60°-62°C.

A solution of 20 g of 1-hydroxy-1-[p-(1-cyclohexenyl)-phenyl]-ethane in 300 ml of absolute benzene is stirred at room temperature in the presence of 10 ml of thionylchloride. The batch is evaporated under vacuum and the crude, oily 1-chloro-1-[p-(1-cyclohexenyl)-phenyl]-ethane dissolved in 50 ml of dimethylsulphoxide and stirred dropwise into a suspension of 15 g of sodium cyanide in 300 ml of dimethylsulphoxide. The batch is stirred for 15 hours at 70°C, then cooled, 400 ml of water are added and the whole is extracted with a 1:1-mixture of ether+ethyl acetate. The extract is dried over magnesium sulphate, filtered and evaporated under vacuum. Distillation of the residue under a high vacuum given α-[p-(1-cyclohexenyl)-phenyl]-propionitrile as a yellow oil which boils at 125°–130°C under 0.1 mm Hg pressure.

EXAMPLE 7

7 g of α-[para-(1-cyclohexenyl)-phenyl]-propionic acid chloride are added dropwise to a solution, cooled to 10°C, of 10 ml of pyridine in 25 ml of ethanol. The mixture is allowed to stand at room temperature for 3 hours, then evaporated under reduced pressure, and the residue is dissolved in ether and the ethereal solution washed with water, 2N-hydrochloric acid, saturated sodium bicarbonate solution and again with water. The ethereal extracts are dried over sodium sulfate and evaporated, then distilled in a high vacuum to yield α-[para-(1-cyclohexenyl)-phenyl]-propionic acid ethyl ester of the formula

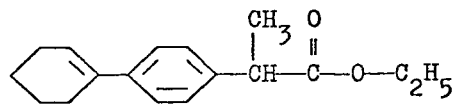

in the form of a colorless oil boiling at 130°–140°C under a pressure of 0.1 mm of Hg.

The α-[para-(1-cyclohexenyl)-phenyl]-propionic acid chloride used as starting material can be prepared as follows:

A solution of 17 g of α-[para-(1-cyclohexenyl)-phenyl]-propionic acid in 100 ml of absolute benzene is treated with 8 ml of thionyl chloride and then heated at 80°–90°C for one hour. The solution is evaporated under reduced pressure, the residue dissolved in 3 × 50 ml of absolute benzene, followed each time by evaporation under reduced pressure. There is thus obtained as residue α-[para-(1-cyclohexenyl)-phenyl]-propionic acid chloride which can be used as it is for the manufacture of the afore-described ester.

EXAMPLE 8

Gaseous ammonia is passed into a solution of 7 g of α-[para-(1-cyclohexenyl)-phenyl]-propionic acid chloride in 100 ml of absolute benzene while stirring at room temperature until saturation is achieved. The batch is then evaporated to dryness, treated with 100 ml of water, and extracted with methylene chloride. The solid residue from the evaporated methylene chloride extract is recrystallized from ethyl acetate+petroleum ether and α-[para-(1-cyclohexenyl)-phenyl]-propionic acid amide of the formula

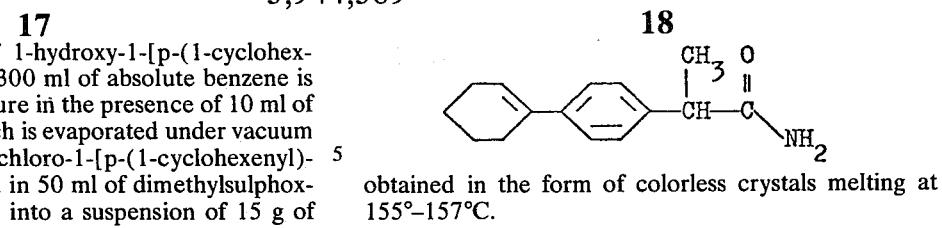

obtained in the form of colorless crystals melting at 155°–157°C.

EXAMPLE 9

A hot solution of 50 g of α-[para-(1-cyclohexenyl)-phenyl]-propionic acid in 1850 ml of ethanol is mixed with a hot solution of 63.9 g of cinchonidine in 1850 ml of ethanol. The mixture is allowed to cool slowly and after 16 hours, the crystals of the cinchonidine salt of the enriched (+)-α-[para-(1-cyclohexenyl)-phenyl]-propionic acid that have precipitated are filtered off. Repeated fractional crystallization according to the usual scheme yields the pure cinchonidine salt of the dextro-rotary acid. In each case the crystals are recrystallized from a 4% ethanolic solution, while the mother liquors which contain mainly the cinchonidine salt of the levorotating acid are caused to crystallize by evaporation to two-thirds of their volumes. The middle fractions are separated by dissolution with the application of heat, and slow cooling.

The pure cinchonidine salt of the dextro-rotating acid is suspended in ether and agitated with 2N-hydrochloric acid until both phases are clear. The ethereal layer is washed with water, dried over sodium sulfate, and evaporated to obtain (+)-α-[para-(1-cyclohexenyl)-phenyl]-propionic acid melting at 101°–102°C; $[\alpha]_D^{20} = +53°C$. (ethanol, c = 1).

In an analogous manner the dextro-rotating acid can be obtained with (−)-α-phenylethylamine instead of cinchonidine.

The fractions which contain practically pure cinchonidine salt of the levo-rotating acid are suspended in ether and agitated with 2N-hydrochloric acid until both phases are clear. The ethereal solution is washed with water, dried over sodium sulfate, and, evaporated. The residue is reacted in hot ethanol with the calculated quantity of (+)-α-phenyl-ethylamine and the resulting salt subjected to fractional crystallization. From the pure fraction, (−)-α-[para-(1-cyclohexenyl)-phenyl]-propionic acid melting at 101°–102°C, $[\alpha]_D^{20} = -53°$, can be isolated.

By heating a 1% solution of an antipode in 2N-sodium hydroxide solution at 100°C for 16 hours, partial racemization is achieved. The optical rotation of the (−) antipode thus drops from −53° to −24°.

EXAMPLE 10

3 g of β-diethylaminoethyl chloride are added to a warm solution of 3 g of the sodium salt of α-[p-(1-cyclohexenyl)-phenyl]-propionic acid in 50 ml of ethanol and 20 ml of dimethylformamide and the whole is allowed to stand for 3 hours. The reaction mixture is then evaporated in vacuo, the residue rendered alkaline with ammonia and extracted with ether. The ethereal residue is dissolved in a little ethanol and treated with ethanolic hydrochloride acid and ether, the hydrochloride of β-diethylamino-ethyl ester of α-[p-(1-cyclohexenyl)-phenyl]-propionic acid of the formula

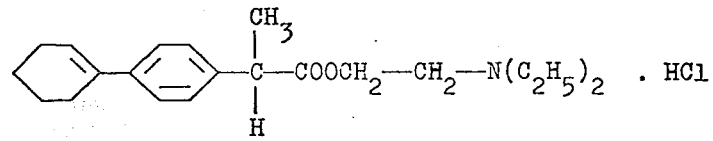

being obtained in the form of colorless crystals melting at 132° – 134°C.

EXAMPLE 11

A solution of 6 g of α-[p-(1-cyclohexenyl)-phenyl]-propionic acid chloride in 10 ml of toluene is added dropwise with stirring at room temperature to a solution of 6 g of β-dimethylamino-ethylamine in 40 ml of toluene. The reaction mixture is stirred for two hours, then extracted with 2N hydrochloric acid, the hydrochloric acid solution washed with ethyl acetate and rendered alkaline with 4N sodium hydroxide solution. The batch is extracted with ethyl acetate, washed with water, dried over sodium sulphate and evaporated in vacuo. The solid residue is recrystallized from methylene chloride and petroleum ether to yield N-(β-dimethylamino-ethyl)-α-[p-(1-cyclohexenyl)-phenyl]-propionic acid amide of the formula

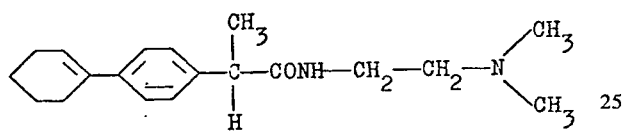

in the form of colorless crystals melting at 77°–78°C. The hydrochloride melts at 123°–126°C.

EXAMPLE 12

A solution of 17 g of silver nitrate in 35 ml of water is added to a solution of 7.1 g of α-[p-(1-cyclohexenyl)-phenyl]-propionic aldehyde in 70 ml of ethanol, and the batch is then treated dropwise with a solution of 10 g of sodium hydroxide in 25 ml of water, the internal temperature being prevented from rising above 45°C by suitable cooling. The batch is stirred for 2 hours at room temperature, filtered through Celite, rinsed with ethanol and the filtrate evaporated to 70 ml. The aqueous alkaline solution is extracted with ether, then acidified with 2N hydrochloric acid and the precipitated acid taken up in methylene chloride. The methylene chloride solution is dried over magnesium sulphate and evaporated and the residue recrystallized from ether, to yield α-[p-(1-cyclohexenyl)-phenyl]-propionic acid as colourless crystals melting at 106° – 108°C. The compound is identical with the acid obtained as described in Example 6.

The α-[p-(1-cyclohexenyl)-phenyl]-propionic aldehyde used as starting material may be prepared as follows:

A solution of sodium ethanolate in ethanol (7.2 g of sodium dissolved in 200 ml of ethanol) is added within 45 minutes dropwise at 0° – 5°C, with stirring, to a solution of 38 g of chloracetic acid ethyl ester and 19.4 g of p-(1-cyclohexenyl)-acetophenone in 200 ml of absolute toluene. Stirring is continued for 16 hours at room temperature, the main quantity of ethanol is evaporated in a rotary evaporater in vacuo, the reaction mixture is diluted with toluene and extracted with ice-water. The toluene layer dried over sodium sulphate and evaporated in vacuo yields a brown oil which is fractionated in a high vacuum. β-Methyl-β-[p-(1-cyclohexenyl)-phenyl]-glycidic acid ethyl ester is obtained in the form of a pale yellow oil boiling at 150° – 155°C under 0.15 mm pressure of mercury.

9.6 g of this ester are dissolved in 40 ml of ethanol and treated with a solution of 0.78 g of sodium in 60 ml of ethanol. 0.72 ml of water is added and the batch is allowed to stand for 20 hours at room temperature. The preciptated sodium salt is filtered off, dissolved in 400 ml of water, adjusted to pH 3 with 2N hydrochloric acid and refluxed under nitrogen for 6 hours. The reaction mixture is cooled, extracted with chloroform, dried over $Na_2SO_4$, evaporated and the oily residue fractionated in a high vacuum. α-[p-(1-cyclohexenyl)-phenyl]-propionic aldehyde, boiling at 178° – 190°C under 0.14 mm pressure of mercury, is obtained.

EXAMPLE 13

A solution of 23 g of α-[p-(1-cyclohexenyl)-phenyl]-butyric acid nitrile and 10 g of potassium hydroxide in 200 ml of ethanol and 80 ml of water is refluxed for 36 hours. The ethanol is evaporated and the residue mixed with 100 ml of water, when a precipitate forms that is recrystallized after filtration from ether and petroleum ether and yields the α-[p-(1-cyclohexenyl)-phenyl]-butyric acid amide of the formula

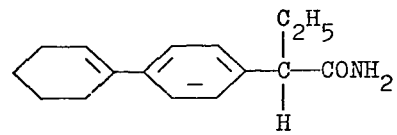

in the form of white crystals melting at 148°–149°C.

The filtered alkaline solution is acidified with 2N hydrochloric acid, extracted with ether and the ethereal extracts are dried over sodium sulphate and evaporated in vacuo. The residue that is recrystallized from petroleum ether yields as main product the α-[p-(1-cyclohexenyl)-phenyl]-butyric acid of the formula

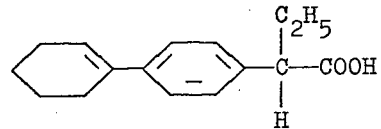

in the form of white crystals melting at 101°–103°C.

The α-[p-(1-cyclohexenyl)-phenyl]-butyric acid nitrile used as starting material can be manufactured as follows:

A solution of 119 g of p-bromo-propiophenone and 100 g of ethylene glycol in 1000 ml of benzene is mixed with 1 ml of concentrated sulphuric acid and refluxed for 10 hours while separating the water that forms. The excess glycol is separated in a separating funnel and the benzene solution washed with sodium carbonate solution and with water. After drying the benzene solution over sodium sulphate, it is evaporated in vacuo to constant weight. The oily residue constitutes the pure 2-(p-bromophenyl)-2-ethyl-1,3-dioxolan that shows no further carbonyl bands in the IR spectrum.

To a well stirred suspension of 5.3 g of magnesium chips, which have been washed with chloroform and activated with iodine, in 150 ml of absolute tetrahydrofuran there is added dropwise at 65°C a solution of 51.4 g of 2-(p-bromo-phenyl)-2-ethyl-1,3-dioxolan in 100 ml of absolute tetrahydrofuran. The dropwise addition is carried out in such a manner that after the onset of the reaction, the temperature does not rise above 65°C.

At the conclusion, a further 50 ml of absolute tetrahydrofuran is added and the reaction mixture heated for one hour to 70°C. It is cooled to 20°C, mixed dropwise with 20 g of cyclohexanone while stirring, and stirred for a further 3 hours at 35°–40°C, then evaporated in vacuo in a rotary evaporater. After recrystallization from ether+petroleum ether, the solid residue yields the 2-[p-(1-hydroxy-cyclohexenyl)-phenyl]-2-ethyl-1,3-dioxolan in the form of a colourless crystalline compound (m.p. 92–93°C).

A solution of 25 g of this compound in 200 ml of glacial acetic acid, 12 ml of concentrated hydrochloric acid and 20 ml of water is heated to 60°–70°C over the course of 1½ hours. The batch is cooled and then mixed with 250 ml of water, when a solid white precipitate forms. The precipitate is filtered off, washed with water, and the crystals are dissolved in methylene chloride and the solution is ddried over sodium sulphate. After evaporation in vacuo, the residue is crystallized from petroleum ether and the p-(1-cyclohexenyl)-propiophenone is obtained in the form of white crystals melting at 78°–79°C.

A solution of 25 g of this ketone in 50 ml of methanol is stirred dropwise into a solution, cooled to 0°C, of 5 g of sodium borohydride in 300 ml of methanol and 40 ml of water. The reaction solution is allowed to stand for 16 hours at room temperature, evaporated to one half its volume and mixed with 100 ml of water. The batch is extracted with methylene chloride, the methylene chloride extracts are washed with water, dried over sodium sulphate and evaporated in vacuo. The oily residue solidifies on standing and constitutes the 1-hydroxy-1-[p-(1-cyclohexenyl)-phenyl]-propane (m.p. 46°–47°C).

20 g of this hydroxy compound is dissolved in 200 ml of benzene, mixed with 100 ml of thionyl chloride and allowed to stand for 2 hours at room temperature, then evaporated in vacuo. A solution of the resulting 1-chloro-1-[p-(1-cyclohexenyl)-phenyl]-propane in 100 ml of dimethylsulphoxide is added to a suspension of 10 g of sodium cyanide in 100 ml of dimethylsulphoxide and heated for 4 hours to 60°C. The batch is cooled, mixed with water and extracted twice on each occasion with 500 ml of a mixture of ether and ethyl acetate (1:1). The organic extracts are dried over sodium sulphate and evaporated to give the crude α-[p-(1-cyclohexenyl)-phenyl]-butyric acid nitrile in the form of a faintly brown oil.

EXAMPLE 14

A solution of 20 g of α-[p-(1-cyclohexenyl)-phenyl]-propionic acid in 150 ml of absolute methanol is mixed with 8 ml of concentrated sulphuric acid and refluxed for 2 hours. The batch is evaporated in vacuo in a rotary evaporator, mixed with ice and water, carefully rendered alkaline with saturated sodium carbonate solution and extracted with ether. The ethereal extracts, which are dried over sodium sulphate and evaporated in vacuo, yield after distillation under a high vacuum the α-[p-(1-cyclohexenyl)-phenyl]-propionic acid methyl ester of the formula

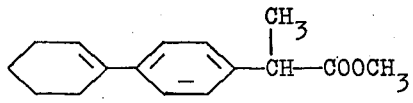

having a boiling point of 140°–145°C (0.1 mm Hg).

EXAMPLE 15

A solution of 4.7 g of hydroxylamine-hydrochloride in 50 ml of absolute methanol is mixed with a solution of 2.3 g of sodium in 50 ml of absolute methanol, cooled to 0°C and filtered off from the precipitated sodium chloride. 8.13 g of α-[p-(1-cyclohexenyl)-phenyl]-propionic acid methyl ester is added to the filtrate and the reaction solution allowed to stand for 16 hours. The batch is then evaporated in vacuo, the solid residue dissolved in 1000 ml of water, mixed with 2N hydrochloric acid until the reaction is acid and extracted with ether. The ethereal extract, which is dried over sodium sulphate and evaporated in vacuo, yields a solid residue from which, by recrystallization from ether+petroleum ether, the α-[p-(1-cyclohexenyl)-phenyl]-propionhydroxamic acid of the formula

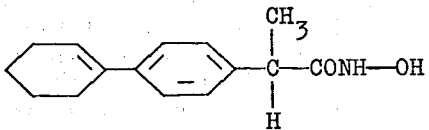

is obtained in the form of a white crystalline substance having a melting point of 145°–146° C.

EXAMPLE 16

Ammonia is introduced via a potassium hydroxide-tower into a 750 ml three-necked flask fitted with a stirring mechanism and a carbon dioxide cooler and which is cooled with an acetone + carbon dioxide bath, until 200 ml of liquid ammonia has collected in it. 1.53 g of sodium is added to the ammonia in small portions and 50 mg of $Fe(NO)_3 \cdot 9 H_2O$ is added to the solution, which has become deep blue. After 15 minutes, the colour of the reaction solution changes to grey-brown. A solution of 14.64 g of α-[p-(1-cyclohexenyl)-phenyl]-propionic acid methyl ester in 20 ml of ether is added dropwise and the reaction mixture stirred for half an hour. Afterwards, the reaction solution is mixed dropwise with a solution of 8.52 g of methyl iodide in 50 ml of ether and allowed to react further for 1½ hours. After adding 3.5 g of ammonium chloride, the ammonia is evaporated, the residue dissolved in methylene chloride and washed with water. The methylene chloride extracts, which are dried over sodium sulphate and evaporated in vacuo, yield after distillation under a high vacuum the α-[p-(1-cyclohexenyl)-phenyl]-isobutyric acid methyl ester of the formula

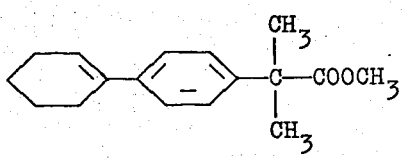

having a boiling point of 150°–155° C (0.05 mm Hg).

EXAMPLE 17

A solution of 11 g of α-[p-(1-cyclohexenyl)-phenyl]-isobutyric acid methyl ester in 100 ml of ethanol is mixed with 20 ml of 10N sodium hydroxide solution and heated for 2 hours to 60°–70° C. This batch is evaporated in vacuo, the residue dissolved in water, washed with ether and the aqueous phase rendered alkaline with 2N hydrochloric acid. Extraction with ether is effected, the ethereal extractes are washed with water, dried over sodium sulphate and evaporated. The solid residue, after recrystallization from ligroin, yields the α-[p-(1-cyclohexenyl)-phenyl]-isobutyric acid of the formula

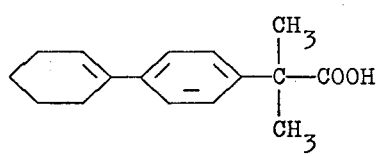

in the form of white crystals (m.p. 142°–144° C).

EXAMPLE 18

To a solution of 21.2 g of 1,2-O-isopropylideneglycerine in 70 ml of absolute pyridine there is added dropwise at 5° C, while stirring, a solution of 40 g of α-[p-(1-cyclohexenyl)-phenyl]-propionic acid chloride in 30 ml of absolute benzene and the mixture allowed to stand for 16 hours at room temperature. The batch is evaporated in vacuo in a rotary evaporator, the residue mixed with ice, extracted with ether and the ether phase washed three times in succession with 100 ml of 2N hydrochloric acid on each occasion, twice with 100 ml of water and once with 100 ml of saturated sodium hydrogen carbonate solution. After drying over sodium sulphate, evaporation in vacuo and distillation under a high vacuum has been effected, the α-[p-(1-cyclohexenyl)-phenyl]-propionic acid-1,2-O-isopropylidene-3-glycerine ester of the formula

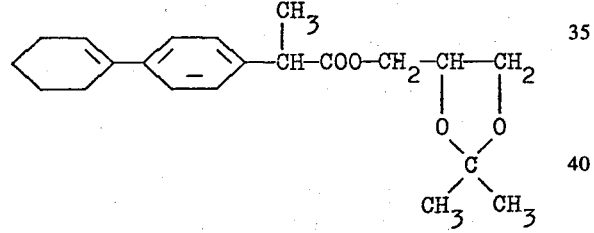

is obtained as an oil having a boiling point of 170°–175° C (0.01 mm Hg).

EXAMPLE 19

A solution of 28 g of α-[p-(1-cyclohexenyl)-phenyl]-propionic acid 1,2-O-isopropylidene-3-glycerine ester in 1500 ml of 60% strength acetic acid is heated for 1 hour to 60° C. The batch is evaporated in vacuo in a rotary evaporator, the residue mixed with ice, rendered alkaline with a saturated sodium hydrogen carbonate solution and extracted with ether. The ethereal extracts, which are washed with water and dried over sodium sulphate, are evaporated in vacuo. On distillation under a high vacuum, the α-[p-(1-cyclohexenyl)-phenyl]-propionic acid-1-glycerine ester of the formula

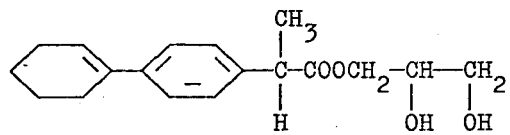

is obtained as a viscous oil having a boiling point of 150° (0.04 mm Hg), and which solidifies to a solid product with a melting point of 50°–52° C.

EXAMPLE 20

A solution of 10 g of α-[p-(1-cyclohexenyl)-phenyl]-propionic acid methyl ester in 50 ml of methanol is mixed with 20 ml of hydrazin hydrate and allowed to stand for 16 hours at room temperature. After the reaction mixture has been evaporated to half its volume, crystallization occurs. The residue is cooled, the crystals that have been deposited are filtered and recrystallized from methylene chloride + petroleum ether, with the α[p-(1-cyclohexenyl)-phenyl]-propionic acid hydrazide of the formula

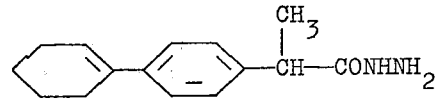

being obtained in the form of white crystals that melt at 127°–128° C.

EXAMPLE 21

A solution of 34 g of α-[p-(1-cyclooctenyl)-phenyl]-propionic acid nitrile in 300 ml of ethanol is mixed with a solution of 16 g of potassium hydroxide in 60 ml of water and refluxed for 36 hours. The ethanol is evaporated in vacuo and the residue dissolved in 350 ml of water. The aqueous solution is first shaken out with ether, then acidified with concentrated hydrochloric acid and extracted once more with ether. The ethereal extract is washed with water, and after being dried over sodium sulphate and evaporated in vacuo, yields a yellow oil. The α-[p-(1-cyclooctenyl)-phenyl]-propionic acid of the formula

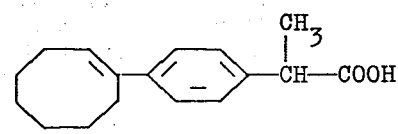

is obtained by distillation under a high vacuum in the of a viscous oil having a boiling point of 190°–195° C (0.1 mm Hg).

The solid sodium salt (m.p. 135°–140° C) is obtained by dissolving this carboxylic acid in ether, mixing the solution with the calculate amount of ethanolic sodium hydroxide, evaporating the mixture, and triturating the residue with acetone.

The α-[p-(1-cyclooctenyl)-phenyl]-propionic acid nitrile used as starting material can be manufactured as follows:

To a well stirred suspension of 31 g of magnesium chips, which have been washed with chloroforme and activated with iodine, in 400 ml of absolute tetrahydrofuran there is added dropwise at 60° C a solution of 244 g of 2-(p-bromophenyl)-2-methyl-1,3-dioxolan in 600 ml of tetrahydrofuran. The dropwise addition is carried out in such a manner that after the onset of the reaction, the temperature does not rise above 60° C. At the conclusion, the reaction mixture is heated for one hour to 60° C, then cooled to 15° C and, while stirring, 164 g of cyclooctanone are added dropwise. After the reaction mixture has been allowed to continue to react for one hour at room temperature, it is evaporated in vacuo. The residue is mixed with ice and 450 ml of a saturated aqueous ammonium chloride solution. After extraction with ether, the ether phases are washed with water, dried over sodium sulphate and evaporated in vacuo. After fractional distillation under a high vacuum, the 2-[p-( 1-hydroxy-cyclooctyl)-phenyl]-2-methyl-1,3-dioxolan is obtained in the form of a colourless, viscous oil having a boiling point of 150°–162° C (0.05 mm Hg).

A solution of 85 g of this compound in 480 ml of glacial acetic acid and 150 ml of 2N hydrochloric acid is heated for one hour to 100° C. The mixture is cooled, evaporated in vacuo, the residue mixed with water and extracted with ether. The ethereal extracts, which are washed with 2N sodium bicarbonate solution, are dried over sodium sulphate and evaporated in vacuo. On distillation under a high vacuum, the p-(1-cyclooctenyl)-acetophenone is obtained as a viscous, light yellow oil having a boiling point of 134°–136° C (0.15 mm Hg).

To a solution, cooled to 0° C, of 14 g of sodium borohydride in 500 ml of methanol and 120 ml of water there is added, while stirring, a solution of 70 g of p-(1-cyclooctenyl)-acetophenone in 200 ml of methanol, and the mixture is stirred for 2 hours at 5°–10° C and allowed to stand for 2 hours at room temperature. After 500 ml of methanol are evaporated in vacuo, the residue is mixed with 500 ml of water and extracted with methylene chloride. The methylene chloride extracts are washed with water, dried over sodium sulphate and evaporated in vacuo. The practically colourless oily residue constitutes the crude 1-hydroxy-1-[p-(1-cyclooctenyl)-phenyl]-ethane, which is then directly processed further.

A solution of 69.2 g of this hydroxy compound in 700 ml of absolute benzene is mixed with 50 ml of thionyl chloride and 5 drops of dimethylformamide, and allowed to stand for 3 hours at room temperature. After the reaction mixture has been evaporated in vacuo, the resulting 1-chloro-1-[p-(1-cyclooctenyl)-phenyl]-ethane is dissolved in 150 ml of dimethylsulphoxide and the solution stirred into a suspension of 34.5 g of sodium cyanide in 200 ml of dimethylsulphoxide that has been heated to 50°–60°C. The mixture is allowed to continue reacting for one hour at this temperature, then cooled, mixed with 300 ml of water and extracted with a mixture of ether + ethyl acetate (1:1). The organic extracts are washed with water, dried over sodium sulphate and evaporated. The residue yields, after distillation under a high vacuum, the α-[p-(1-cyclooctenyl)-phenyl]-propionic acid nitrile in the form of a yellow oil having a boiling point of 165°–172° C (0.15 mm Hg).

EXAMPLE 22

A solution of 5 g of p-(1-cyclohexenyl)-phenylacetonitrile in 100 ml of absolute ethanol is cooled to −10° C. During the course of one hour, dry HCL gas is introduced, while stirring, into the solution, which is left to stand for 16 hours, then evaporated in vacuo in a rotary evaporator to a volume of 30 ml. The reddish coloured alcoholic solution is poured into 100 ml of saturated sodium carbonate solution, which has been mixed with 100 g of ice, and the mixture is extracted twice with 150 ml of ether on each occasion. The ether solution is washed first with saturated sodium chloride solution, then extracted with 100 ml of ice cold 2N H₂SO₄. The sulphonic acid extract is heated for 30 minutes at 60° C on the water bath, in the course of which a colourless oil separates. The aqueous solution is shaken out with ether, the ethereal extracts are washed with water, dried over sodium sulphate, filtered and evaporated. The residue is distilled under a high vacuum and the ethyl p-(1-cyclohexenyl)-phenylacetate of the formula

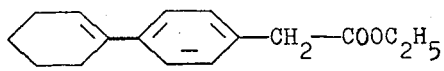

is obtained in the form of a colourless oil having a boiling point of 130°–135° C (0.5 mm Hg).

The p-(1-cyclohexenyl)-phenyl-acetonitrile used in this Example as starting material can be prepared in the following way:

To a solution of 7 g of p-(1-cyclohexenyl)-phenylbromide in 100 ml of absolute ether there is added at 5° C, while stirring and in an atmosphere of nitrogen, 50 ml of a solution of 4.3 g of n-butyl-lithium in absolute ether. The mixture is allowed to reach room temperature, stirred for 30 minutes at 30° C, then cooled to 20° C and a solution of 4 g of N-methyl-N-formyl-aniline in 50 ml of absolute ether is added dropwise, when the internal temperature rises to 30° C. After the reaction mixture has been allowed to continue to react for 30 minutes at room temperature, it is poured into 100 ml of ice cold 2N hydrochloric acid and extracted with ether. The ether layers are washed with water, dried over sodium sulphate and evaporated in vacuo. The residue is distilled under a high vacuum and yields the p-(1-cyclohexenyl)-benzaldehyde having a boiling point of 110°–120° C (0.2 mm Hg).

1 g of sodium borohydride is added to a solution, cooled to 0° C, of 5 g of this aldehyde in 30 ml of methanol and 10 ml of water, while stirring. The mixture is stirred for 15 minutes at 5° C, 150 ml of water are added and the batch extracted with methylene chloride. The methylene chloride residue is distilled under a high vacuum, and the p-(1-cyclohexenyl)-benzylalcohol having a boiling point of 120°–125° C (0.1 mm Hg) is obtained which, after recrystallization from ether + petroleum ether, melts at 70°–71° C.

A solution of 4 g of this alcohol in 50 ml of toluene is mixed with 1 ml of thionyl chloride and heated for 10 minutes to 80° C. The batch is evaporated in vacuo, the oily p-(1-cyclohexenyl)-benzylchloride dissolved in 30 ml of dimethylsulphoxide and added to a stirred suspension, heated to 50° C, of 2 g of pulverized, dry sodium cyanide in 50 ml of dimethylsulphoxide. The mixture is allowed to continue to react for 2 hours at 70° C, then poured into 150 ml of water, extracted with ether, and the residue is distilled under a high vacuum. The solid p-(1-cyclohexenyl)-phenyl-acetonitrile having a boiling point of 145° C (0.15 mm Hg) is thus obtained, which melts at 71°–73° C after recrystallization from petroleum ether.

The p-(1-cyclohexenyl)-benzaldehyde described in this Example as intermediate can also be manufactured as follows:

A solution of 22.9 g of 2-(p-bromophenyl)-1,3-dioxolan in 100 ml of tetrahydrofuran is added dropwise, at 60° C, to a well stirred suspension of 2.65 g of magnesium chips, which have been washed with chloroform and activated with iodine, in 100 ml of absolute tetrahydrofuran. The dropwise addition is carried out in such a manner that after the onset of the reaction, the temperature does not rise above 60° C. At the conclusion, the reaction mixture is heated for one hour, then cooled to 30° C and, while stirring, 11 g of cyclohexanone are added dropwise. After being heated for 1 hour to 50° C, the reaction mixture is evaporated in vacuo in a rotary evaporator and the residue mixed with ice and a saturated ammonium chloride solution. Extraction with ether is effected, and the ethereal extracts are dried over sodium sulphate and evaporated. The residue is distilled under a high vacuum and yields the 2-[p-(1-hydroxy-cyclohexyl)-phenyl]-1,3-dioxolan having a boiling point of 160°–170° C (0.05 mm Hg), which becomes solid on standing and melts at 95°–97° C after recrystallization from ether + petroleum ether.

A solution of 10 g of this compound in 30 ml of glacial acetic acid is mixed with 3 ml of concentrated hydrochloric acid and 5 ml of water and heated for one hour in an atomsphere of nitrogen at 100° C. After being cooled to room temperature, the batch is mixed with ice and extracted with ether. The ethereal extracts are washed with saturated sodium bicarbonate solution and with water, dried over sodium sulphate and evaporated. The residue yields, after distillation under a high vacuum, the p-(1-cyclohexenyl)-benzaldehyde having a boiling point of 110°–120° C (0.2 mm Hg).

EXAMPLE 23

A solution of 2 g of ethyl p-(1-cyclohexenyl)-phenylacetate in 50 ml of ethanol is mixed with 15 ml of 2N NaOH and heated for 2 hours to 60° C. After the bulk of the ethanol has been distilled off in vacuo, the residue is mixed with 20 ml of water, acidified with 2N hydrochloric acid and extracted with ether. The ethereal extracts are dried over sodium sulphate, filtered and evaporated. The solid residue is recrystallized from petroleum ether and yields the p-(1-cyclohexenyl)-phenyl-acetic acid of the formula

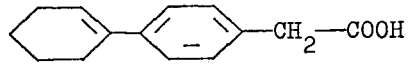

in the form of colourless crystals (m.p. 120°–121° C).

EXAMPLE 24

A solution of 13 g of p-(1-cyclohexenyl)-phenylthioacetomorpholide in 30 ml of glacial acetic acid is mixed with 5 ml of concentrated sulphuric acid and 6 ml of water, and heated for 4 hours at 100° C. The batch is then cooled to 0° C, adjusted with 4N sodium hydroxide solution to pH 8, evaporated in vacuo in a rotary evaporator, the residue mixed with water and activated charcoal, filtered and acidified with 4N hydrochloric acid. Extraction with ether is effected, the ethereal extracts are dried over sodium sulphate, filtered and evaporated in vacuo. The solid residue is recrystallized from ether + petroleum ether and the p-(1-cyclohexenyl)-phenyl-acetic acid of the melting point 118°–120° C is obtained which is identical with the compound obtained as described in Example 23.

The p-(1-cyclohexenyl)-phenyl-thioacetomorpholide used in this Example as starting material, can be manufactured as follows:

A mixture of 20 g of p-(1-cyclohexenyl)-acetophenone, 9 g of morpholine and 3.5 g of sulphur is heated for one hour at 100° C and for 15 minutes at 150° C. The mixture is then cooled, mixed with ethanol, and the crystals that have been deposited are filtered. After recrystallization twice from ethanol + petroleum ether, the p-(1-cyclohexenyl)-phenyl-thioacetomorpholide of the formula

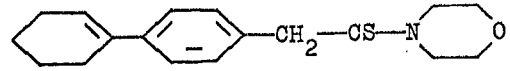

is obtained in the form of crystals that melt at 154–156° C.

EXAMPLE 25

A solution of 5 g of α-[3-chloro-4-(1-cyclohexenyl)-phenyl]-propionic acid nitrile and 5 g of potassium hydroxide in 200 ml of ethanol and 50 ml of water is boiled for 15 hours under reflux. After evaporation of the ethanol in vacuo, the aqueous residue is extracted with ether. After the ether phase has been dried over sodium sulphate and evaporated in vacuo, the solid residue is recrystallised from ether-petroleum ether, whereby α-[3-chloro-4-(1-cyclohexenyl)-phenyl]-propionic acid amide of formula

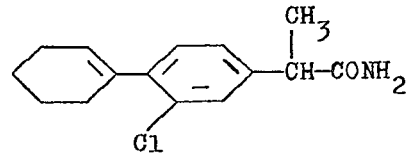

is obtained as colourless crystals of melting point 125°–125° C.

The aqueous alkaline phase is clarified by filtration through diatomaceous earth (Hyflo), acidified with 2 N hydrochloric acid and extracted with ether. The ether extract is washed with water, dried over sodium sulphate and evaporated in vacuo. The oily residue is dissolved in petroleum ether, the solution is treated with active charcoal and filtered, and the filtrate is concentrated in vacuo. On standing, crystallisation occurs. The mixture is filtered and α-[3-chloro-4-(1-cyclohexenyl)-phenyl]-propionic acid of formula

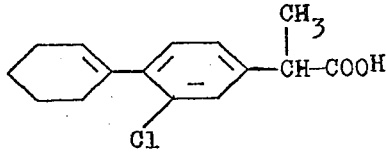

is thus obtained as colourless crystals of melting point 97°–99° C.

The sodium salt is obtained by dissolving this carboxylic acid in the calculated amount of ethanolic sodium hydroxide solution and evaporating in vacuo.

The α-[3-chloro-4-(1-cyclohexenyl)-phenyl]propionic acid nitrile used as the starting material in this example can be manufactured as follows:

A mixture of 19.8 g of 4-bromo-3-chlor-acetophenone, 18.5 g of ethylene glycol, 500 ml of toluene and 0.2 ml of concentrated sulphuric acid is boiled for 2 hours under reflux in an apparatus provided with a water separator, care being taken for the water formed to be separated off periodically. After cooling to room temperature, the toluene solution is extracted by shaking with saturated sodium bicarbonate solution and with water, and is dried over sodium sulphate and evaporated in vacuo. The oily residue is distilled in a high vacuum and 2-(4-bromo-3-chlorophenyl)-2-methyl-1,3-dioxolane of boiling point 85°–93° C (0.03 mm Hg) is thus obtained as a pale yellow oil.

65 ml of a 1.5 N solution of butyl-lithium in ether are added dropwise over the course of 60 minutes, whilst stirring and under a nitrogen atmosphere, to a solution, cooled to −70° C, of 27.7 g of 2-(4-bromo-3-chlorophenyl)-2-methyl-1,3-dioxolane in 500 ml of absolute ether. After the mixture has been allowed to continue reacting for 30 minutes at −70° C, 9.8 g of cyclohexanone are added dropwise over the course of 15 minutes. The reaction solution is brought to room temperature and stirred for a further 30 minutes at 30° C. It is then treated with ice and with saturated ammonium chloride solution, and the ether layer is washed with ice-cold 2 N hydrochloric acid. The ether extract is dried over sodium sulphate, evaporated in vacuo, and fractionated in a high vacuum. The fraction which distils within the range of 190°–210° C (0.1 mm Hg) represents the crude 2-[ 3-chloro-4-(1-hydroxy-1-cyclohexyl)-phenyl]-2-methyl-1,3-dioxolane.

9 g of this compound are boiled for one hour under reflux with 150 ml of glacial acetic acid and 50 ml of concentrated hydrochloric acid. After cooling to room temperature, the mixture is diluted with 200 ml of water and extracted with ether. The ether extracts are dried over sodium sulphate and evaporated in vacuo. The oily residue is fractionated in a high vacuum. The fraction which distils at 140°–145° C (0.1 mm Hg) represents 3-chloro-4-(1-cyclohexenyl)-acetophenone.

7 g of 3-chloro-4-(1-cyclohexenyl)-acetophenone are added in portions, whilst stirring, to a solution of 1 g of sodium borohydride in 100 ml of methanol and 20 ml of water, cooled to 0° C. The mixture is stirred for a further 2 hours at 10° C, treated with ice and water, and extracted with methylene chloride. The methylene chloride extracts are washed with water, dried over sodium sulphate and evaporated in vacuo. The residue represents crude 1-hydroxy-1-[3-chloro-4-(1-cyclohexenyl)-phenyl]-ethane.

A solution of 7 g of this hydroxy compound in 150 ml of absolute benzene is mixed with 2 ml of thionyl chloride and the mixture is boiled for 5 minutes under reflux. It is left to stand for a further 2 hours at room temperature and then evaporated in vacuo. The residue consists of 1-chloro-1-[3-chloro-4-(cyclohexenyl)-phenyl]-ethane.

A solution of 8 g of this compound in 20 ml of dimethylsulphoxide is added dropwise, whilst stirring, to a suspension of 2 g of sodium cyanide in 30 ml of dimethylsulphoxide, warmed to 70° C. After the mixture has been allowed to react for a further 30 minutes at 110° C, the reaction mixture is poured into 300 ml of ice water and extracted with ether. The ether extracts are washed with water, dried over sodium sulphate and evaporated in vacuo. After evaporation in vacuo, crude α-[3-chloro-4-(1-cyclohexenyl)-phenyl]-propionic acid nitrile is obtained and this can be directly used for the hydrolysis described above.

EXAMPLE 26

In an analogous manner as described in Example 9 α-[meta-chloro-para-(1-cyclohexenyl)-phenyl]-propionic acid can be resolved into its levorotatory and dextrorotatory forms.

EXAMPLE 27

Tablet containing 20 mg of the sodium salt of α-[p-(1-cyclohexenyl)-phenyl]-propionic acid may be prepared, for example, with the following ingredients:

| Ingredients | Per tablet |
|---|---|
| Active substance | 20.0 mg |
| Wheat starch | 45.0 mg |
| Lactose | 60.0 mg |
| Colloidal silicic acid | 5.0 mg |
| Talc | 9.0 mg |
| Magnesium stearate | 1.0 mg |
| | 140.0 mg |

Method

The active substance is mixed with part of the wheat starch, with lactose and colloidal silicic acid, and the mixture passed through a sieve. A further part of the wheat starch is pasted with 5 times the quantity of water on a water-bath and the powdery mixture kneaded with this paste until a weakly plastic mass is formed. The plastic mass is passed through a sieve of about 3 mm mesh, dried, and the dried granulate passed through a sieve. The remaining wheat starch, talc and magnesium stearate are added. The resulting mixture is compressed into tablets weighing 140 mg.

EXAMPLE 28

In an analogous manner as described in the Examples 1–8 and 10-25 the following compounds may be prepared:

α-[para-(1-cyclobutenyl)-phenyl]-butyric acid methyl ester,

α-[ortho-(4-dimethylamino-1-cyclohexenyl)-phenyl]-propionic acid,

α-[ortho-(3-chlor-1-cyclohexenyl)-phenyl]-acrylic acid-benzyl ester,

α-[para-(3-chlor-1-cyclohexenyl)-meta-ethoxy-phenyl]-crotonic acid mono-methylamide, α-[para-(4-brom-1-cyclohexenyl)-meta-trifluoromethyl-phenyl]-cinnamic acid-cyclohexyl ester, α-[para-(4-oxo-1-cyclohexenyl)-meta-chloro-phenyl]-β-phenyl-propionic acid-diisopropylamide, α-[para-(4-allyloxy-1-cyclohexenyl)-meta-nitro-phenyl]-isobutyric acid, α-[para-(1-cycloocytenyl)-phenyl]-propionic acid-morpholide, α-[para-(1-cyclohexenyl)-meta-amino-phenyl]-propionic acid-N-methylpiperazide-hydrochloride, α-[para-(2-chloro-1-cyclohexenyl)-phenyl]-propionic acid, α-[para-(1-cyclohexenyl)-ortho-fluoro-phenyl]-propionic acid, α-[para-(1-cyclohexenyl)-meta-methyl-phenyl]-propionic acid-penta-methylene-amide, α-[para-(1-cyclohexenyl)-meta-chloro-phenyl]-propionic acid-tert.butyl-ester, α-[para-(1-cyclohexenyl)-phenyl]-isobutyric acid, α-[para-(1-cyclohexenyl)-phenyl]-isovaleric acid, α-[para-(1-cyclohexenyl)-phenyl]-β-(para-chloro-phenyl)-propionic acid, para-(1-cyclopentenyl)-phenylacetic acid, α-[para-(4-methyl-1-cyclohexenyl)-phenyl]-isobutyric acid, α-[meta-chloro-para-(1-cyclohexenyl)-phenyl]-propion-hydroxamic acid.

EXAMPLE 29

14 g of methylamine is added to 24.4 g of α-[(1-cyclohexenyl)-phenyl]-propionic acid methyl ester in 100 ml of absolute ethanol and the reaction mixture heated in an autoclave for 30 hours to 140° C. The batch is evaporated to dryness in vacuo, the residue dissolved in 200 ml of methylene chloride, and extracted with 100 ml of N hydrochloric acid. The organic phase, which is washed with water, until neutral and dried over sodium sulphate, is evaporated in vacuo. The α-[p-(1-cyclohexenyl)-phenyl]-propionic acid methyl amide of the formula

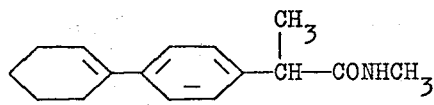

is crystallized from methanol + water in the form of small, glistening disc-shaped crystals which melt at 118°–120°.

I claim:

1. A member selected from the group consisting of compounds of the formula

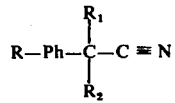

in which $Ph$ stands for a member selected from the group consisting of ortho-phenylene, ortho-phenylene substituted by a member selected from the group consisting of lower alkyl, lower alkoxy, halogen, trifluoromethyl, amino, nitro and hydroxy, para-phenylene and paraphenylene substituted by a member selected from the group consisting of lower alkyl, lower alkoxy, halogen, trifluoromethyl, amino, nitro and hydroxy, R stands for a member selected from the group consisting of 1-cycloalkenyl having 4–8 ring carbon atoms and 1-cycloalkenyl having 4–8 ring carbon atoms substituted by a member selected from the group consisting of lower alkyl, lower alkoxy, lower alkenyloxy, hydroxy, oxo, amino, mono-lower alkylamino, di-lower alkylamino, lower alkyleneamino, lower oxaalkyleneamino, lower thiaalkyleneamino and lower azaalkyeneamino and $R_1$ and $R_2$ each stands for a member selected from the group consisting of hydrogen, lower alkyl, lower alkenyl, lower alkinyl, phenyl-lower alkyl, phenyl-lower alkyl substituted by a member selected from the group consisting of lower alkyl, lower alkoxy, halogen and trifluoromethyl, phenyl-lower alkenyl and phenyllower alkenyl substituted by a member selected from the group consisting of lower alkyl, lower alkoxy, halogen and trifluoromethyl, and when taken together $R_1$ and $R_2$ stand for lower alkylidene.

2. A compound as claimed in claim 1, in which Ph stands for a member selected from the group consisting of para-phenylene and meta-halogeno-para-phenylene, $R_2$ stands for hydrogen, $R_1$ for methyl and R stands for a member selected from the group consisting of 1-cyclopentenyl, 1-cyclohexenyl and 1-cycloheptenyl.

3. A compound as claimed in claim 1 and being the α-[p-(1-cyclohexenyl)-phenyl]-propionitrile.

* * * * *